(12) United States Patent
Delijani et al.

(10) Patent No.: US 11,496,083 B2
(45) Date of Patent: Nov. 8, 2022

(54) DEVICES AND METHODS FOR CONTROLLING ELECTROMECHANICAL ACTUATORS

(71) Applicant: MEDTRONIC MINIMED, INC., Northridge, CA (US)

(72) Inventors: Fatemeh Delijani, Chatsworth, CA (US); Adam S. Trock, Simi Valley, CA (US); Seth N. Kazarians, Duarte, CA (US); Jalal Elidrissi, Santa Clarita, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 538 days.

(21) Appl. No.: 16/685,734

(22) Filed: Nov. 15, 2019

(65) Prior Publication Data

US 2021/0151161 A1 May 20, 2021

(51) Int. Cl.
*H02P 27/08* (2006.01)
*H02P 6/08* (2016.01)
(Continued)

(52) U.S. Cl.
CPC .......... *H02P 27/08* (2013.01); *A61M 5/1456* (2013.01); *A61M 5/14244* (2013.01);
(Continued)

(58) Field of Classification Search
CPC .... H02P 7/00; H02P 7/02; H02P 7/025; H02P 7/04; H02P 7/05; H02P 7/20; H02P 7/22; H02P 7/29; H02P 7/295; H02P 8/00; H02P 29/00; H02P 1/00; H02P 1/04; H02P 1/16; H02P 1/18; H02P 1/24; H02P 1/26; H02P 1/42; H02P 1/46; H02P 1/465; H02P 1/54; H02P 1/56; H02P 1/58; H02P 3/00; H02P 3/08; H02P 3/18; H02P 6/00; H02P 6/24; H02P 6/32; H02P 21/00; H02P 25/00; H02P 25/03; H02P 25/034; H02P 25/06;
(Continued)

(56) References Cited

U.S. PATENT DOCUMENTS 4,562,751 A 1/1986 Nason et al.
4,685,903 A 8/1987 Cable et al.
(Continued)

FOREIGN PATENT DOCUMENTS

EP 3370336 A1 9/2018

OTHER PUBLICATIONS

International Search Report and Written Opinion of International Application No. PCT/US2020/057311, dated Feb. 3, 2021, 11 pp.

*Primary Examiner* — Antony M Paul
(74) *Attorney, Agent, or Firm* — Shumaker & Sieffert, P.A.

(57) ABSTRACT

Electromechanical actuation systems and related operating methods are provided. A method of controlling an electromechanical actuator in response to an input command signal at an input terminal involves determining a commanded actuation state value based on a characteristic of the input command signal, generating driver command signals based on the commanded actuation state value and an actuator type associated with the electromechanical actuator, and operating driver circuitry in accordance with the driver command signals to provide output signals at output terminals coupled to the electromechanical actuator.

20 Claims, 7 Drawing Sheets

(51) Int. Cl.
*H02P 27/06* (2006.01)
*G16H 20/17* (2018.01)
*A61M 5/142* (2006.01)
*A61M 5/145* (2006.01)
*A61M 5/168* (2006.01)

(52) U.S. Cl.
CPC ........ *A61M 5/16831* (2013.01); *G16H 20/17* (2018.01); *H02P 6/08* (2013.01); *H02P 27/06* (2013.01); *A61M 2005/14208* (2013.01); *A61M 2205/3365* (2013.01)

(58) Field of Classification Search
CPC ...... H02P 25/064; H02P 25/066; H02P 27/00; H02P 27/08; H02P 27/085
See application file for complete search history.

(56) References Cited

U.S. PATENT DOCUMENTS

| | | |
|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,088,608 A | 7/2000 | Schulman et al. |
| 6,119,028 A | 9/2000 | Schulman et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,589,229 B1 | 7/2003 | Connelly et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,740,072 B2 | 5/2004 | Starkweather et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,827,702 B2 | 12/2004 | Lebel et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,323,142 B2 | 1/2008 | Pendo et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 10,576,220 B2 * | 3/2020 | Armes ................ A61M 5/3287 |
| 2006/0031094 A1 | 2/2006 | Cohen et al. |
| 2007/0123819 A1 | 5/2007 | Mernoe et al. |
| 2010/0160861 A1 | 6/2010 | Causey, III et al. |
| 2013/0154540 A1 | 6/2013 | Koo |
| 2013/0253419 A1 | 9/2013 | Favreau |
| 2013/0338630 A1 | 12/2013 | Agrawal et al. |
| 2014/0066889 A1 | 3/2014 | Grosman et al. |
| 2018/0169334 A1 | 6/2018 | Grosman et al. |

* cited by examiner

DEVICES AND METHODS FOR CONTROLLING ELECTROMECHANICAL ACTUATORS

TECHNICAL FIELD

Embodiments of the subject matter described herein relate generally to medical devices, and more particularly, embodiments of the subject matter relate to extensible actuator control modules with improved reliability and reduced size suitable for use in a portable electronic device, such as a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Different infusion pump devices may have different form factors, constraints, or otherwise utilize different techniques, which result in the particular type of actuator most suitable for the drive system varying from one type of infusion pump device to the next. Often, this also entails using a different controller that is designed or otherwise configured for use with a particular type of actuator. Alternatively, a common type of microcontroller or similar processing module could be utilized across different devices and actuators by being programmed to support the particular type of actuator deployed therewith; however, this often requires a sufficient number of general purpose input/output terminals to support the different potential types of actuators, which, in turn, increases the size of the microcontroller package. Accordingly, it is desirable to provide an actuator control module that is extensible for use with different types of actuators without the drawbacks associated with existing approaches. Other desirable features and characteristics will become apparent from the subsequent detailed description and the appended claims, taken in conjunction with the accompanying drawings and this background.

BRIEF SUMMARY

Electromechanical actuation devices, systems, and methods suitable for use in medical devices or systems, such as an infusion device or infusion system, are provided. An embodiment of an electromechanical actuator driver module includes a terminal to receive an input command signal, command logic coupled to the terminal to convert the input command signal to an actuation command, and decoding logic coupled to the command logic to generate a driver command for a selected type of electromechanical actuator based on the actuation command.

In another embodiment, an apparatus for a driver module is provided that includes an input terminal to receive an input command signal having a duty cycle, a plurality of output terminals to be coupled to an electromechanical actuator, driver circuitry coupled to the plurality of output terminals, duty cycle measurement logic coupled to the input terminal to measure the duty cycle to obtain a commanded actuation state value, and duty cycle decoding logic coupled to the duty cycle measurement logic and the driver circuitry to convert the commanded actuation state value to a driver command for the electromechanical actuator and provide the driver command to the driver circuitry, wherein the driver circuitry provides output signals at the plurality of output terminals in accordance with the driver command.

In another embodiment, a method of controlling an electromechanical actuator in response to an input command signal at an input terminal is provided. The method involves determining a commanded actuation state value based on a characteristic of the input command signal, generating driver command signals based on the commanded actuation state value and an actuator type associated with the electromechanical actuator, and operating driver circuitry in accordance with the driver command signals to provide output signals at output terminals coupled to the electromechanical actuator.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes an electromechanical actuator, exemplary embodiments of the subject matter described herein are implemented in conjunction with medical devices, such as portable electronic medical devices. Although many different applications are possible, the following description focuses on embodiments that incorporate a fluid infusion device (or infusion pump) as part of an infusion system deployment. That said, the subject matter described herein is not limited to infusion devices (or any particular configuration or realization thereof) and may be implemented in an equivalent manner in the context of multiple daily injection (MDI) therapy regimen or other medical devices, such as continuous glucose monitoring (CGM) devices, injection pens (e.g., smart injection pens), and the like. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Generally, a fluid infusion device includes a motor or other actuation arrangement that is operable to displace a plunger (or stopper) or other delivery mechanism to deliver a dosage of fluid, such as insulin, from a reservoir provided within the fluid infusion device to the body of a patient. Dosage commands that govern actuation may be generated in an automated manner in accordance with the delivery control scheme associated with a particular operating mode, and the dosage commands may be generated in a manner that is influenced by a current (or most recent) measurement of a physiological condition in the body of the user. For example, in a closed-loop operating mode, dosage commands may be generated based on a difference between a current (or most recent) measurement of the interstitial fluid glucose level in the body of the user and a target (or reference) glucose value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

As described in greater detail below primarily in the context of FIGS. 3-5, exemplary embodiments described herein employ an electromechanical actuation module that is extensible and capable of supporting any number of different types of electromechanical actuators. In this regard, the electromechanical actuation module may be deployed across different types or configurations of fluid infusion devices that use different types of electromechanical actuators (e.g., brushless direct current (BLDC) motors, brushed direct current (BDC) motors, stepper motors, shape-memory alloy actuators, etc.). The electromechanical actuation module includes an individual input terminal for receiving an input command signal and command logic circuitry that maps or otherwise converts the input command signal to a commanded actuation. The electromechanical actuation module also includes decoding logic that is coupled to the command logic circuitry that generates a corresponding driver command for achieving the commanded actuation for the particular type of actuator that the electromechanical actuation module. The driver command is provided to driver circuitry of the electromechanical actuation module, which, in turn generates corresponding output voltage signals that are applied or otherwise provided to the appropriate inputs of the electromechanical actuator. In this regard, the driver command generated by the decoding logic and the corresponding output voltage signals for a given commanded actuation state will vary depending upon the selected type of actuator to be supported.

In exemplary embodiments, the input command signal is realized as a pulse-width modulation (PWM) voltage signal having a variable duty cycle. The command logic circuitry measures the width (or duration) of the duty cycle and thereby converting the duty cycle into a discrete digital representation that is provided to the decoding logic. In exemplary embodiments, electromechanical actuation module includes additional safety logic that disables additional actuation when the input command signal is maintained constant, for example, by providing a commanded actuation state value that results in the driver circuitry grounding or otherwise providing a high impedance at the inputs of the electromechanical actuator. This eliminates the need for a dedicated enable signal for the electromechanical actuation module while also preventing a runaway condition that could otherwise result if an anomalous condition resulted in a static input command signal.

Figure 1:
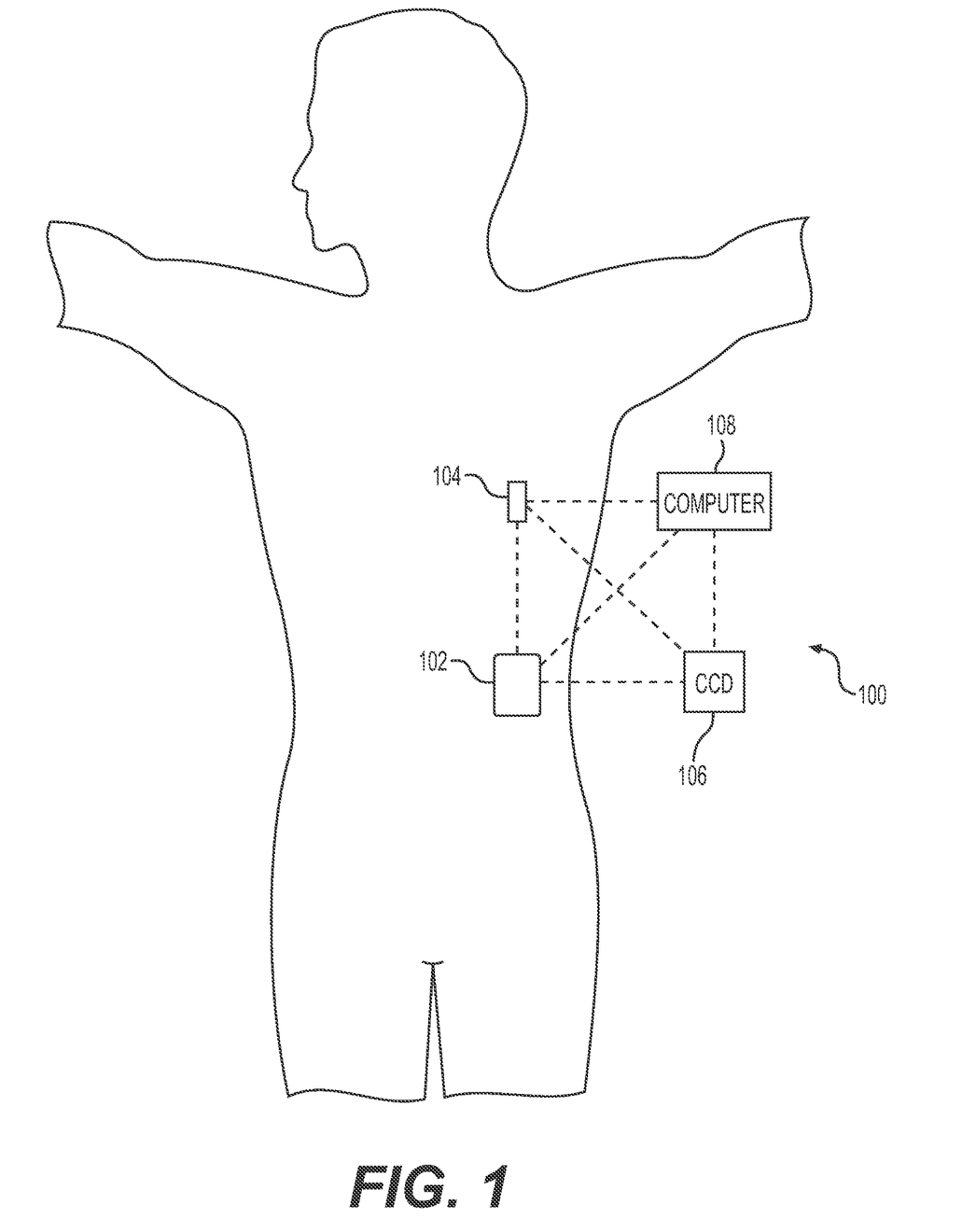
FIG. 1 depicts an exemplary embodiment of an infusion system.

FIG. 1 depicts one exemplary embodiment of an infusion system 100 that includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other medicament into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

In some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402,153 or United States Patent Application Publication No. 2014/0066889, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
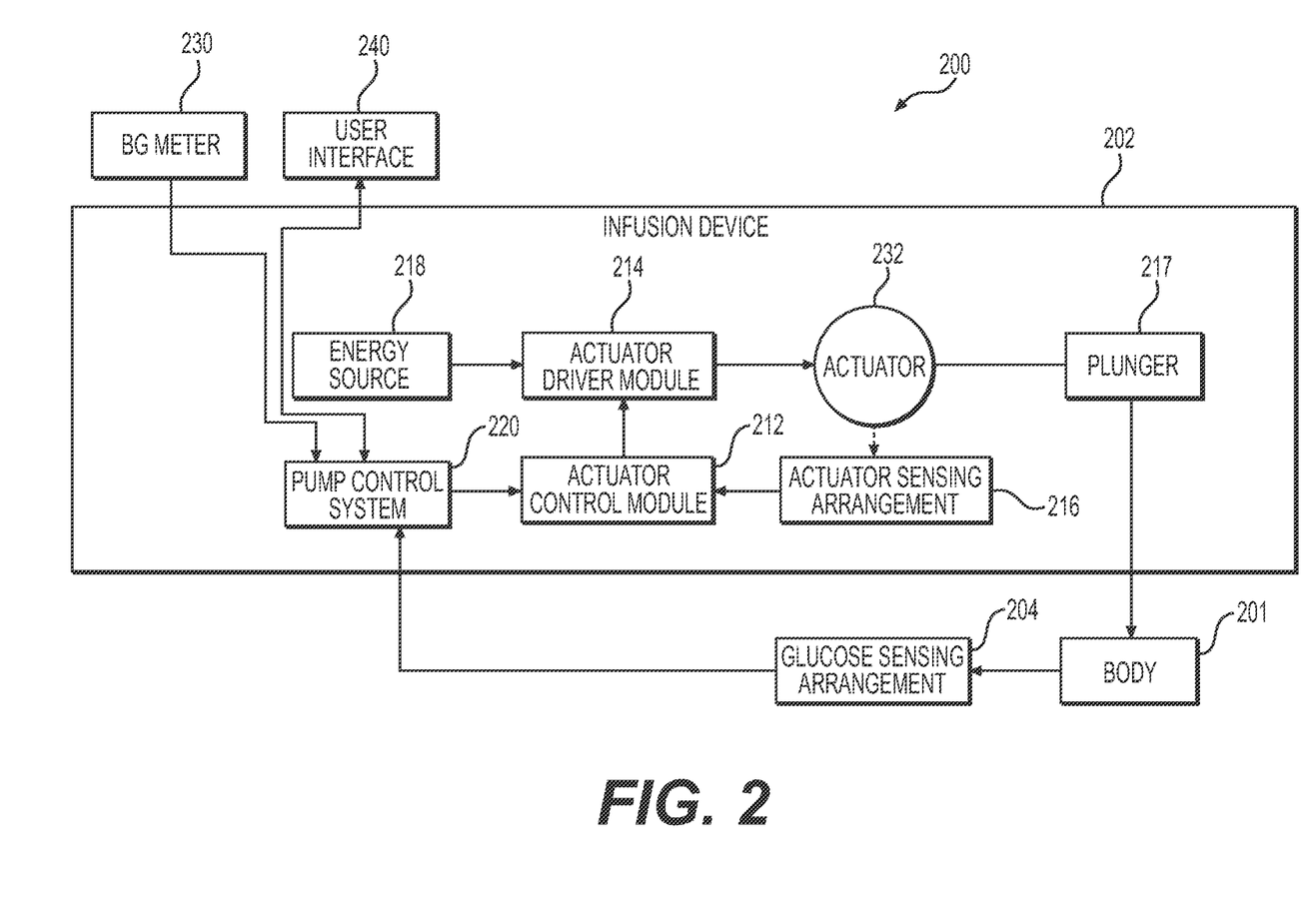
FIG. 2 is a block diagram of an exemplary control system suitable for use with a fluid infusion device in one or more embodiments.

FIG. 2 depicts an exemplary embodiment of a control system 200 suitable for use with an infusion device 202, such as the infusion device 102 described above. The control system 200 is capable of controlling or otherwise regulating a physiological condition in the body 201 of a patient to a desired (or target) value or otherwise maintain the condition within a range of acceptable values in an automated or autonomous manner. In one or more exemplary embodiments, the condition being regulated is sensed, detected, measured or otherwise quantified by a sensing arrangement 204 (e.g., sensing arrangement 104) communicatively coupled to the infusion device 202. However, it should be noted that in alternative embodiments, the condition being regulated by the control system 200 may be correlative to the measured values obtained by the sensing arrangement 204. That said, for clarity and purposes of explanation, the subject matter may be described herein in the context of the sensing arrangement 204 being realized as a glucose sensing arrangement that senses, detects, measures or otherwise quantifies the patient's glucose level, which is being regulated in the body 201 of the patient by the control system 200.

In exemplary embodiments, the sensing arrangement 204 includes one or more interstitial glucose sensing elements that generate or otherwise output electrical signals (alternatively referred to herein as measurement signals) having a signal characteristic that is correlative to, influenced by, or otherwise indicative of the relative interstitial fluid glucose level in the body 201 of the patient. The output electrical signals are filtered or otherwise processed to obtain a measurement value indicative of the patient's interstitial fluid glucose level. In some embodiments, a blood glucose meter 230, such as a finger stick device, is utilized to directly sense, detect, measure or otherwise quantify the blood glucose in the body 201 of the patient. In this regard, the blood glucose meter 230 outputs or otherwise provides a measured blood glucose value that may be utilized as a reference measurement for calibrating the sensing arrangement 204 and converting a measurement value indicative of the patient's interstitial fluid glucose level into a corresponding calibrated blood glucose value. For purposes of explanation, the calibrated blood glucose value calculated based on the electrical signals output by the sensing element(s) of the sensing arrangement 204 may alternatively be referred to herein as the sensor glucose value, the sensed glucose value, or variants thereof.

Although not illustrated in FIG. 2, practical embodiments of the control system 200 may include one or more additional sensing arrangements configured to sense, detect, measure or otherwise quantify a characteristic of the body of the patient that is indicative of a condition in the body of the patient. For example, in addition to the glucose sensing arrangement 204, one or more auxiliary sensing arrangements may be worn, carried, or otherwise associated with the body 201 of the patient to measure characteristics or conditions that may influence the patient's glucose levels or insulin sensitivity, such as a heart rate sensor (or monitor), a lactate sensor, a ketone sensor, an acceleration sensor (or accelerometer), an environmental sensor, and/or the like.

In the illustrated embodiment, the pump control system 220 generally represents the electronics and other components of the infusion device 202 that control operation of the fluid infusion device 202 according to a desired infusion delivery program in a manner that is influenced by the sensed glucose value indicating the current glucose level in the body 201 of the patient. For example, to support a closed-loop operating mode, the pump control system 220 maintains, receives, or otherwise obtains a target or commanded glucose value, and automatically generates or otherwise determines dosage commands for operating an electromechanical actuator 232 (e.g., a BLDC motor, a BDC motor, a stepper motor, a shape-memory alloy actuators, or the like) to displace the plunger 217 and deliver insulin to the body 201 of the patient based on the difference between the sensed glucose value and the target glucose value. In other operating modes, the pump control system 220 may generate or otherwise determine dosage commands configured to maintain the sensed glucose value below an upper glucose limit, above a lower glucose limit, or otherwise within a desired range of glucose values. In practice, the infusion device 202 may store or otherwise maintain the target value, upper and/or lower glucose limit(s), insulin delivery limit(s), and/or other glucose threshold value(s) in a data storage element accessible to the pump control system 220. As described in greater detail, in one or more exemplary embodiments, the pump control system 220 automatically adjusts or adapts one or more parameters or other control information used to generate commands for operating the electromechanical actuator 232 in a manner that accounts for a likely change in the patient's glucose level or insulin response resulting from a meal, exercise, or other activity.

Still referring to FIG. 2, the target glucose value and other threshold glucose values utilized by the pump control system 220 may be received from an external component (e.g., CCD 106 and/or computing device 108) or be input by a patient via a user interface element 240 associated with the infusion device 202. In practice, the one or more user interface element(s) 240 associated with the infusion device 202 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 240 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the patient. It should be noted that although FIG. 2 depicts the user interface element(s) 240 as being separate from the infusion device 202, in practice, one or more of the user interface element(s) 240 may be integrated with the infusion device 202. Furthermore, in some embodiments, one or more user interface element(s) 240 are integrated with the sensing arrangement 204 in addition to and/or in alternative to the user interface element(s) 240 integrated with the infusion device 202. The user interface element(s) 240 may be manipulated by the patient to operate the infusion device 202 to deliver correction boluses, adjust target and/or threshold values, modify the delivery control scheme or operating mode, and the like, as desired.

Still referring to FIG. 2, in the illustrated embodiment, the infusion device 202 includes an actuator control module 212 coupled to an electromechanical actuator driver module 214, which, in turn, is coupled to the electromechanical actuator 232 that is operable to displace a plunger 217 in a reservoir and provide a desired amount of fluid to the body 201 of a patient. In this regard, displacement of the plunger 217 results in the delivery of a fluid, such as insulin, that is capable of influencing the patient's physiological condition to the body 201 of the patient via a fluid delivery path (e.g., via tubing of an infusion set). The electromechanical actuator driver module 214 is coupled between an energy source 218 and the electromechanical actuator 232, and the actuator control module 212 generates or otherwise provides command signals that operate the electromechanical actuator driver module 214 to provide current (or power) from the energy source 218 to the electromechanical actuator 232 to displace the plunger 217 in response to receiving, from a pump control system 220, a dosage command indicative of the desired amount of fluid to be delivered.

In exemplary embodiments, the energy source 218 is realized as a battery housed within the infusion device 202 that provides direct current (DC) power. In this regard, the electromechanical actuator driver module 214 generally represents the combination of logic circuitry, hardware and/or other electrical components configured to convert or otherwise transfer DC power provided by the energy source 218 into alternating electrical signals applied to inputs of the electromechanical actuator 232 (e.g., respective phases of the stator windings of a motor) that result in current flow that causes the electromechanical actuator 232 to displace the plunger 217. For example, the actuator driver module 214 may generate voltage signals applied to the phases of stator windings of a motor that result in current flow through the stator windings that generates a stator magnetic field and causes a rotor of the motor to rotate.

The actuator control module 212 is configured to receive or otherwise obtain a commanded dosage from the pump control system 220, convert the commanded dosage to a commanded translational displacement of the plunger 217, and command, signal, or otherwise operate the electromechanical actuator driver module 214 to cause actuation of the electromechanical actuator 232 by an amount that produces the commanded translational displacement of the plunger 217. For example, the actuator control module 212 may determine an amount of rotation of the rotor required to produce translational displacement of the plunger 217 that achieves the commanded dosage received from the pump control system 220. The actuator control module 212 monitors the current actuation state indicated by the output of a sensing arrangement 216 (e.g., the rotational position (or orientation) of the rotor with respect to the stator of a motor that is indicated by a rotor sensing arrangement) and provides one or more command signals to the actuator driver module 214 until achieving the desired amount of actuation, and thereby the desired delivery of fluid to the patient.

For example, using a BLDC motor as the actuator 232, the actuator control module 212 receives the current rotor position measurement data from the sensing arrangement 216 and determines the desired rotor configuration or orientation corresponding to the desired delivery of fluid relative to the current rotor position using a lookup table. The actuator control module 212 then provides a PWM voltage signal to the actuator driver module 214 having a fixed frequency with a duty cycle that corresponds to the desired rotor position using another lookup table. As the measured rotor position changes, the actuator control module 212 dynamically updates the duty cycle of the PWM voltage signal as appropriate to move the rotor position from one state to another in the desired manner. For example, the actuator control module 212 may provide the PWM voltage signal with a duty cycle of 10% to move the rotor to an orientation of 30 degrees, followed by a duty cycle of 20% to move the rotor from the orientation of 30 degrees to an orientation of 60 degrees. Once the rotor reaches the desired position, the actuator control module 212 may maintain the duty cycle at the percentage corresponding to that position to hold or otherwise maintain the rotor at that particular angular orientation.

As described in greater detail below in the context of FIGS. 3-5, in exemplary embodiments, the actuator control module 212 provides an input voltage signal having a duty cycle corresponding to an angle of rotation of the electromechanical actuator 232 (and corresponding displacement of the plunger 217) for achieving the commanded rotation angle. In such embodiments, the actuator driver module 214 needs only a single input terminal for receiving the input command signal from the actuator control module 212. The actuator driver module 214 includes logic configured to convert the input duty cycle into the appropriate electrical signals to be applied to the electromechanical actuator 232 to achieve the desired actuation (or commutation) state corresponding to the input duty cycle and then applies those electrical signals to the inputs of the electromechanical actuator 232. For example, where the electromechanical actuator 232 is realized as a BLDC motor, the actuator driver module 214 applies voltage signals to commutate the respective phases of the stator windings at the appropriate orientation of the rotor magnetic poles with respect to the stator and in the appropriate order to provide a rotating stator magnetic field that rotates the rotor in the desired direction by the commanded amount.

In some embodiments, after the actuator control module 212 operates the electromechanical actuator driver module 214 and/or electromechanical actuator 232 to achieve the commanded rotation angle, the actuator control module 212 ceases operating the electromechanical actuator driver module 214 and/or electromechanical actuator 232 until a subsequent rotation angle command is received. As described in greater detail below in the context of FIGS. 3-4 and 6, to put the electromechanical actuator 232 into an idle state, the actuator control module 212 may provide a fixed or constant input command signal (e.g., a duty cycle of 0% or 100%), which, in turn, results in the electromechanical actuator driver module 214 allowing the inputs of the electromechanical actuator 232 to be grounded or otherwise enter a high impedance state during which the electromechanical actuator driver module 214 effectively disconnects or isolates the electromechanical actuator 232 from the energy source 218.

Depending on the embodiment, the actuator control module 212 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In exemplary embodiments, the actuator control module 212 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the actuator control module 212. The computer-executable programming instructions, when read and executed by the actuator control module 212, cause the actuator control module 212 to perform or otherwise support the tasks, operations, functions, and processes described herein.

It should be appreciated that FIG. 2 is a simplified representation of the infusion device 202 for purposes of explanation and is not intended to limit the subject matter described herein in any way. In this regard, depending on the embodiment, some features and/or functionality of the sensing arrangement 204 may implemented by or otherwise integrated into the pump control system 220, or vice versa. Similarly, in practice, the features and/or functionality of the actuator control module 212 may implemented by or otherwise integrated into the pump control system 220, or vice versa. Furthermore, the features and/or functionality of the pump control system 220 may be implemented by control electronics located in the fluid infusion device 202, while in alternative embodiments, the pump control system 220 may be implemented by a remote computing device that is physically distinct and/or separate from the infusion device 202, such as, for example, the CCD 106 or the computing device 108.

Figure 3:
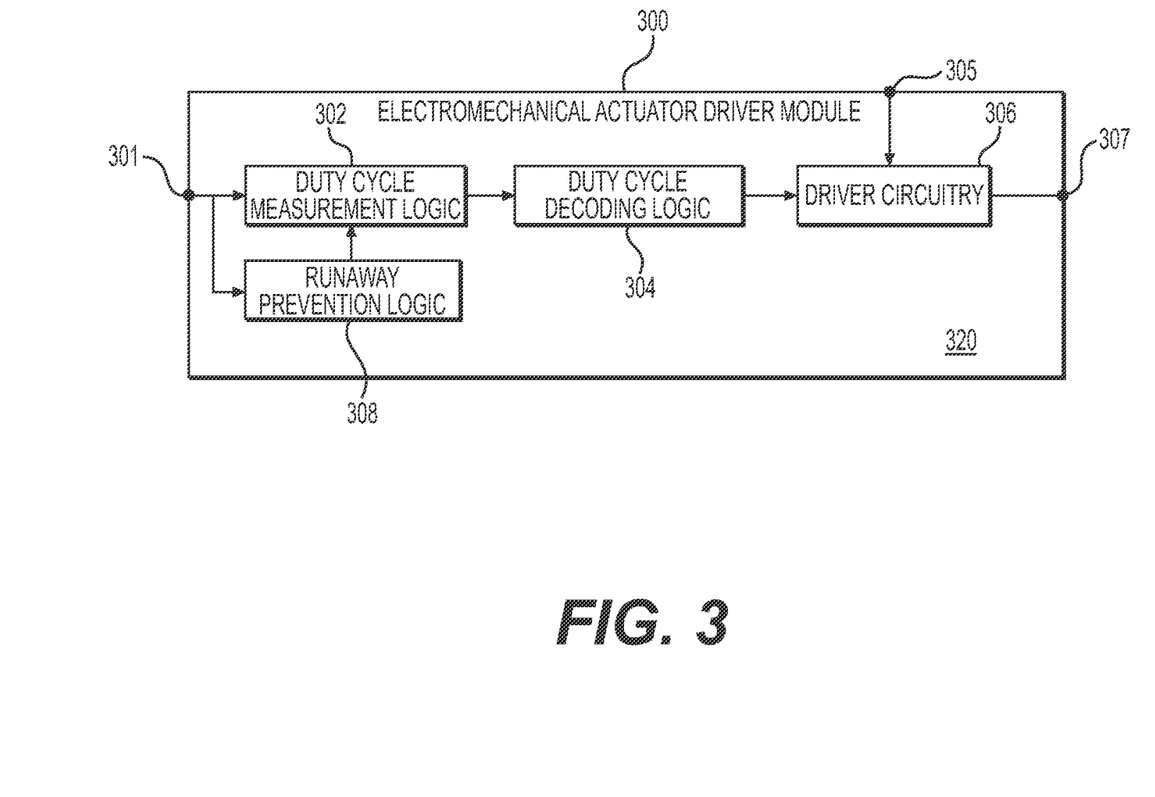
FIG. 3 is a block diagram of an exemplary electromechanical actuator driver module suitable for use in the infusion device in the control system of FIG. 2 in one or more embodiments.

FIG. 3 depicts an exemplary embodiment of an electromechanical actuator driver module 300 suitable for use with any number of different types of electromechanical actuators. In this regard, the electromechanical actuator driver module 214 may be utilized as an electromechanical actuator driver module 214 in an infusion device 202 with any number of different types of electromechanical actuators 232. It should be appreciated that FIG. 3 is a simplified representation of the electromechanical actuator driver module 300 for purposes of explanation and is not intended to limit the subject matter described herein in any way.

In exemplary embodiments, the electromechanical actuator driver module 300 includes, without limitation, input command logic circuitry 302 (alternatively referred to herein as duty cycle measurement logic) that maps or otherwise converts an input command signal at an input command terminal 301 to a commanded actuation state, decoding logic circuitry 304 (alternatively referred to herein as duty cycle decoding logic) coupled to the input command logic circuitry 302 to map or otherwise convert the commanded actuation state into appropriate driver command signals for the particular type of electromechanical actuator being utilized, and driver circuitry 306 coupled to the decoding logic circuitry 304 to generate electrical output signals at one or more output terminals 307 coupled to corresponding inputs of the electromechanical actuator in response to the driver command signals from the decoding logic circuitry 304. For example, the driver circuitry 306 may be realized using any sort of driver or power conversion circuitry (e.g., H-bridges, power inverters, or the like) to modulate or otherwise regulate current flow between a supply voltage input terminal 305 and the one or more output terminals 307. The electromechanical actuator driver module 300 also includes additional safety logic 308 (alternatively referred to herein as runaway prevention logic) that is coupled to the input command terminal 301 and the input command logic circuitry 302 to disable actuation based on the input command signal, as described in greater detail below.

In one or more exemplary embodiments, the logic components 302, 304, 306, 308 of the electromechanical actuator driver module 300 are encapsulated or otherwise contained within a common housing or device package 320. For example, the logic components 302, 304, 306, 308 may all formed or otherwise provided on a common substrate or support structure for the electromechanical actuator driver module 300, such as, for example, a printed circuit board or similar electronics substrate, a lead frame or die pad, or the like. The terminals 301, 305, 307 generally represent the input/output interfaces of the actuator driver device package 320 and may be realized using any sort of pin, pad, connector, port, and/or the like. In this regard, in exemplary embodiments where the input command signal is realized as a voltage signal having a variable duty cycle, the actuator driver device package 320 needs to include only a signal input terminal 301 for receiving the input command signal. Additionally, by virtue of the safety logic 308 disabling actuation in response to a static duty cycle, the actuator driver device package 320 does not need to include an additional or separate terminal for an enable input signal. Additionally, the number of output terminals 307 may be limited to the maximum number of inputs from among the different types of electromechanical actuators to be supported. For example, in one or more embodiments, the driver circuitry 306 includes four half H-bridge arrangements, with each half H-bridge arrangement being coupled between the input voltage terminal 305 and a respective output terminal 307, such that the electromechanical actuator driver module 300 includes a total of four output terminals 307 capable of supporting a bipolar stepper motor, in addition to supporting three-phase BLDC motors, three-phase BDC motors, or shape-memory alloy actuation arrangements having fewer than four inputs (or actuators).

Figure 4A:
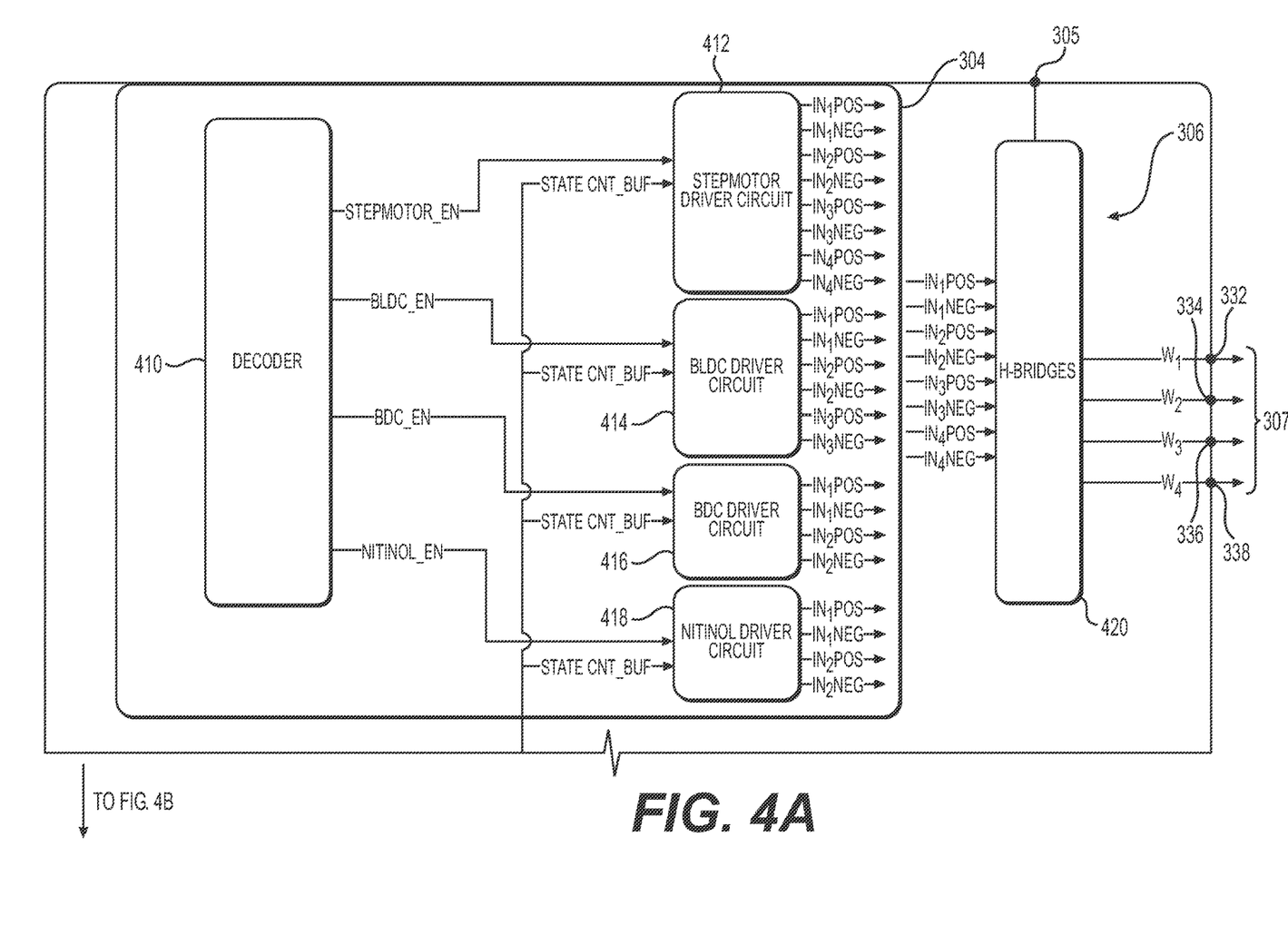
FIGS. 4A-4B depict a schematic view of an electromechanical actuator driver module such as the electromechanical actuator driver module of FIG. 3 in accordance with one or more exemplary embodiments.
Figure 4B:
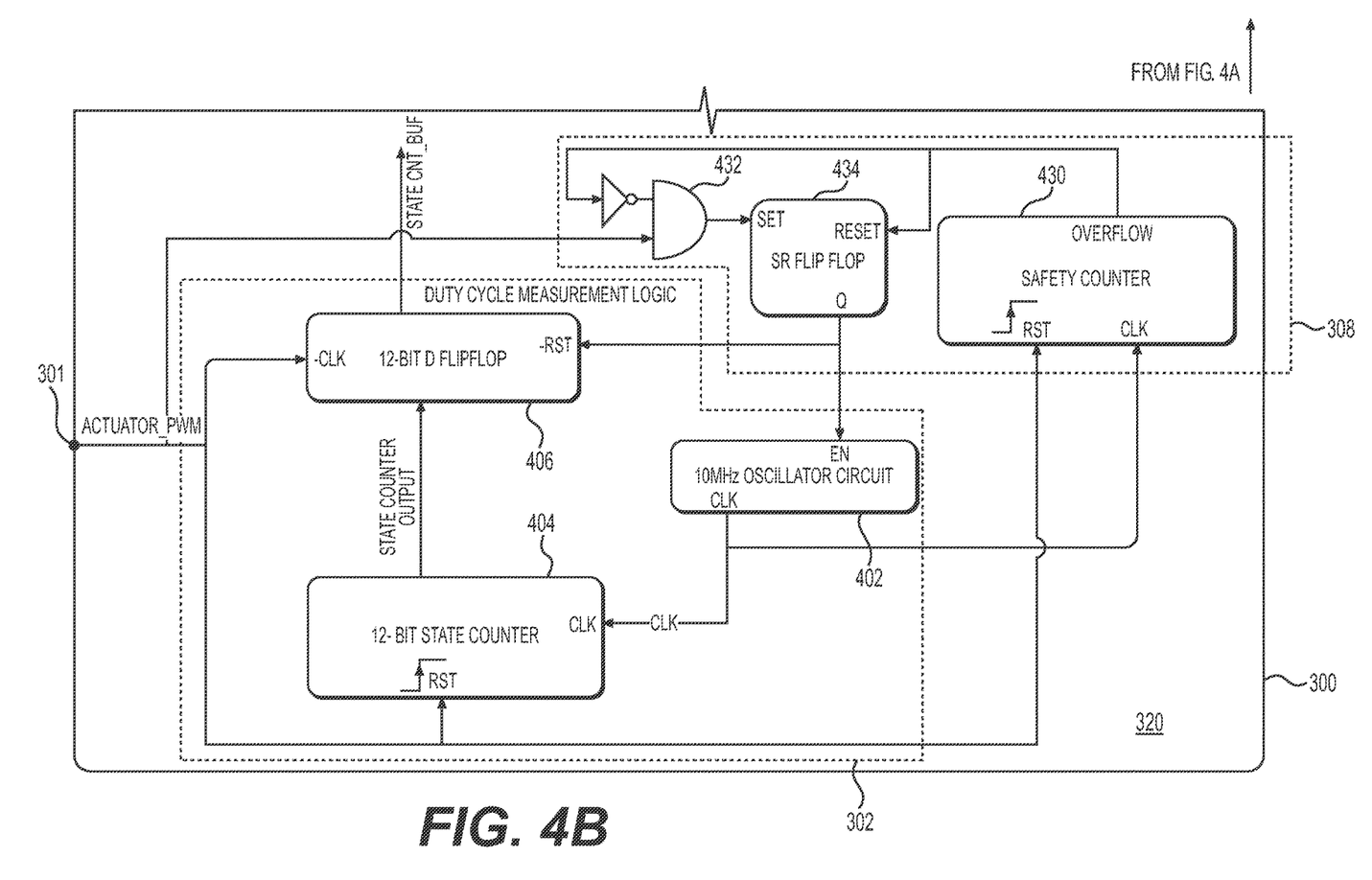

Referring now to FIGS. 4A-4B with continued reference to FIG. 3, in exemplary embodiments, the input command logic circuitry 302 is configured to measure the width or duration of the duty cycle and maps the corresponding percentage of an electrical cycle to a discrete digital value that is provided to the decoding logic 304. The duty cycle measurement logic 302 includes oscillator circuitry 402 configured to generate or otherwise provide a digital clock signal having a fixed frequency (e.g., 10 MHz). In exemplary embodiments, the frequency of the digital clock signal is greater than the frequency of the input command signal. For example, in one or more embodiments, the frequency of the digital clock signal is greater than the frequency of the input command signal by at least a factor of 1000 (e.g., a clock frequency of 10 MHz and an input command signal frequency of 10 kHz or less). The clock signal output by the oscillator circuitry 402 is provided to a clock input of a counter 404, which, in exemplary embodiments is realized as a 12-bit state counter. The reset input of the counter 404 is connected to the input command terminal 301, such that a logical high voltage level for the input duty cycle command signal resets the value of the counter 404 at the beginning of each new cycle for the input duty cycle command signal. The output of the counter 404 is coupled to the input to data (D) flip-flop circuitry 406 that is configured to latch the output of the counter 404 when the input duty cycle command signal transitions to a logical low voltage level (e.g., by providing the logical inverse of the input command signal to the clock input(s) of the D flip-flop circuitry 406). Thus, the counted value by the counter 404 and latched by the D flip-flop circuitry 406 corresponds to the duration of the duty cycle of the logical high voltage level at the input terminal 301.

The illustrated duty cycle decoding logic 304 includes multiple different driver command modules 412, 414, 416, 418, with each driver command modules 412, 414, 416, 418 corresponding to a different type of electromechanical actuator to be supported by the electromechanical actuator driver module 300. In this regard, each driver command module 412, 414, 416, 418 includes an enable input that is coupled to or otherwise connected to a corresponding output of a decoder 410 that is utilized to select the particular type of electromechanical actuator being utilized. For example, in the illustrated embodiment with four driver command modules 412, 414, 416, 418, the decoder 410 may be realized as a 2-to-4 line decoder that provides a logical high voltage signal at the output coupled to the stepper motor driver command module 412 and logical low voltage signals at the outputs coupled to the other driver command modules 414, 416, 418 in response to a selection input of 00, a logical high voltage signal at the output coupled to the BLDC motor driver command module 414 and logical low voltage signals at the outputs coupled to the other driver command modules 412, 416, 418 in response to a selection input of 01, and so on. In some embodiments, the selection input(s) to the decoder 410 is hardwired to permanently select a particular type of electromechanical actuator to be supported for a given deployment of the electromechanical actuator driver module 300. That said, in other embodiments, the selection input(s) to the decoder 410 may be coupled to corresponding selection input terminal(s) of the device package 320 of the electromechanical actuator driver module 300 to allow the selected type of electromechanical actuator coupled to the output terminals 307 to vary.

The latched state count value output by the D flip-flop circuitry 406 represents a commanded actuation corresponding to the measured duty cycle of the input command signal. The commanded actuation state count value is provided to a corresponding input of each of the driver command modules 412, 414, 416, 418. Each of the driver command modules 412, 414, 416, 418 includes logic, circuitry, hardware and/or other electrical components configured to generate driver command signals corresponding to the commanded actuation count value for their respective type of electromechanical actuator, as described in greater detail below in the context of FIG. 5. In this regard, the enabled driver command module 412, 414, 416, 418 maps or otherwise converts the latched commanded actuation state count value provided by the D flip-flop circuitry 406 into corresponding driver command signals that are output by the respective driver command module 412, 414, 416, 418 and provided to inputs of the driver circuitry 305.

Based on the driver command signals input to the driver circuitry 305, the driver circuitry 306 selectively enables the supply voltage from the supply voltage terminal 305 to be provided to one or more of the output terminals 307, thereby enabling resultant current flow to the electromechanical actuator to actuate the electromechanical actuator. For example, as described above, in an exemplary embodiment, the driver circuitry 306 includes an H-bridge arrangement 420 including four half H-bridges corresponding to the four output terminals 307, where each half H-bridge is operated to selectively couple its respective output terminal 307 to either the supply voltage terminal 305 or a ground (or negative) reference voltage node according to the driver command signals applied to the switches of the respective half H-bridge.

The runaway prevention logic 308 includes a safety counter 430 having a clock input that receives the clock signal output by the oscillator circuitry 402. The reset input to the safety counter 430 is coupled to the input command terminal 301, such that a logical high voltage level for the input duty cycle command signal resets the value of the safety counter 430 at the beginning of each new cycle for the input duty cycle command signal. An overflow output of the safety counter 430 is inverted and provided to the input of an AND gate 432 that outputs the logical conjunction of the inverse of the overflow output bit and the input duty cycle command signal. The output of the AND gate 432 is provided to the set input of a set-reset (SR) flip-flop 434 having its reset input coupled to the overflow output of the safety counter 430 and its output coupled to the enable input of the oscillator circuitry 402. Thus, during normal operation, when the input command signal varies between logical high and low voltage levels, the safety counter 430 does not overflow, the output of the AND gate 432 is a logical high voltage whenever the input command signal has a logical high voltage, thereby enabling the oscillator circuitry 402 and corresponding operation of the duty cycle measurement logic 302. In one or more embodiments, the safety counter 430 is configured to overflow when the input command signal is constant for at least one and a half electrical cycles.

When the input command signal at the input terminal 301 has a duty cycle of either 0% or 100% for a sufficient duration to cause the safety counter 308 to overflow (e.g., greater than one and a half electrical cycles), the SR flip-flop 434 is reset, thereby disabling the oscillator circuitry 402. Additionally, the reset input of the D flip-flop circuitry 406 receives the inverse of the output of the SR flip-flop 434, which results in the D flip-flop circuitry 406 resetting and providing a commanded actuation state value of zero to the driver command modules 412, 414, 416, 418. In exemplary embodiments, the driver command modules 412, 414, 416, 418 are configured to generate driver command signals in response to an input value of zero that result in the driver circuitry 306 allowing the output terminals 307 to be grounded or otherwise enter a high impedance state. For example, in response to a commanded actuation state value of zero, each of the driver command modules 412, 414, 416, 418 may be configured to provide driver command signals that result in each of the switching elements of the H-bridge arrangement 420 being opened or otherwise turned off to prevent current flow through the H-bridge arrangement 420 and effectively provide a high impedance, thereby allowing the output terminals 307 to float as the electromechanical actuator coasts to a stop. Thus, referring to FIG. 2, when the actuator control module 212 determines the actuation has been sufficient to achieve the desired dosage command, the actuator control module 212 may provide a constant logical low voltage signal (e.g., a duty cycle of zero) to the input terminal 301 of the electromechanical actuator driver module 214, 300 to cease further actuation of the electromechanical actuator 232 without having to assert or de-assert a dedicated enable/disable signal for the electromechanical actuator 232. Additionally, the runaway prevention logic 308 protects against any potential anomalous conditions where the actuator control module 212 might inadvertently maintain a logical high voltage level at the input command terminal 301.

Figure 5:
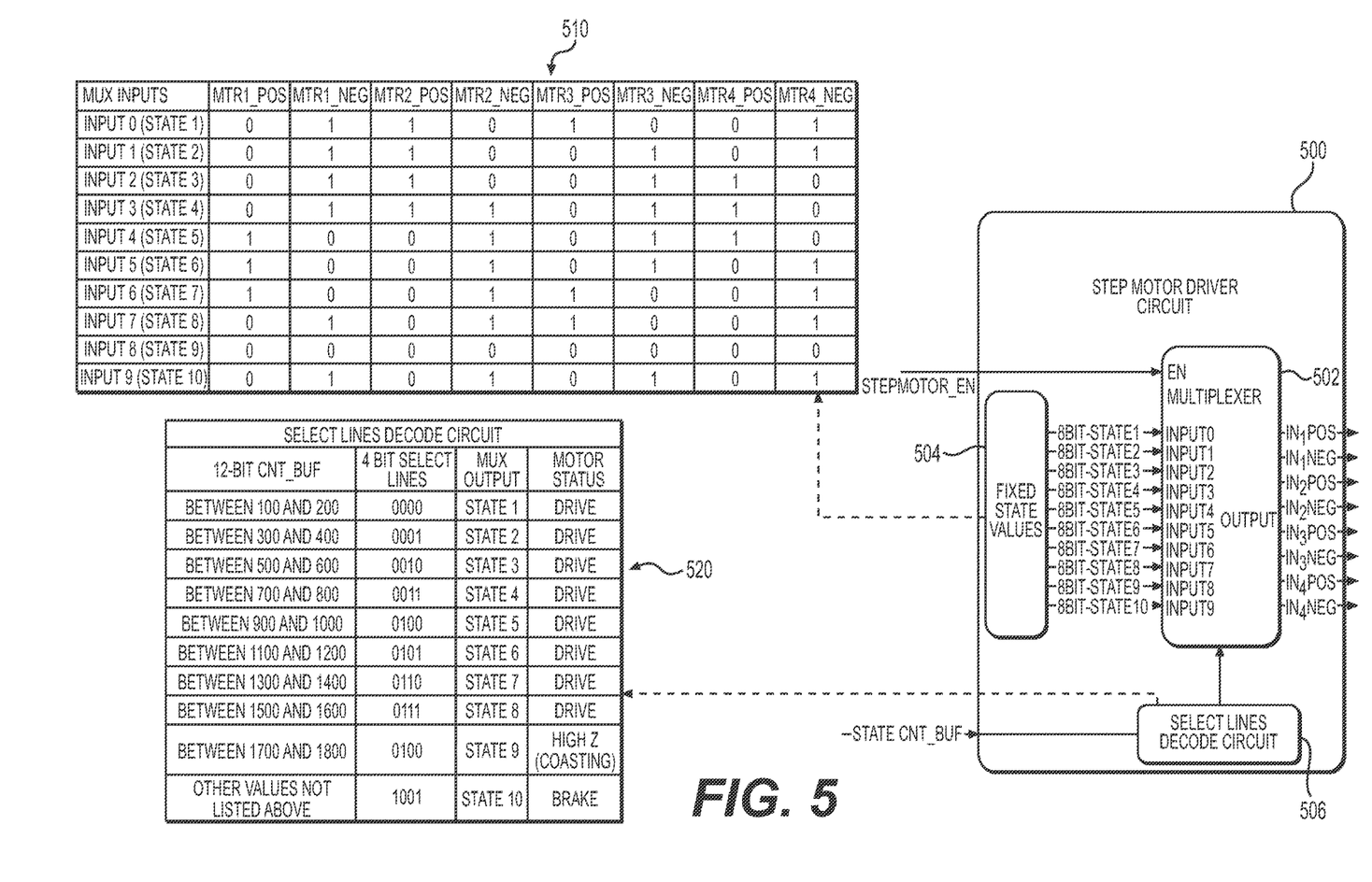
FIG. 5 is a schematic view of a driver command module suitable for use in the electromechanical actuator driver module of FIG. 4A in one or more exemplary embodiments.

FIG. 5 depicts an exemplary embodiment of a stepper motor driver command module 500 suitable for use as the stepper motor driver command module 412 in the duty cycle decoding logic 304 in the electromechanical actuator driver module 214, 300 described above in one or more embodiments. The stepper motor driver command module 500 includes a multiplexer 502 configured to selectively provide a selected 8-bit input value provided from one of the 8-bit inputs to the multiplexer 502 to the corresponding 8-bit outputs of the multiplexer 502, which, in turn may be coupled to the respective switching elements of the four half H-bridge arrangement 420 to selectively open or close the respective switching elements according to the respective bit line coupled to the activation input of the respective switching element. The enable input of the multiplexer 502 is coupled to the corresponding enable output of the decoder 410 to allow the output of the stepper motor driver command module 500 to be enable when a stepper motor is utilized (or otherwise disabled).

The respective inputs of the multiplexer 502 may be coupled to a hardware data storage arrangement 504 configured to maintain fixed state values that represent the appropriate operation of the driver circuitry 306 (e.g., the switches of the H-bridge arrangement 420) for achieving different commutation states for the stepper motor. For example, the hardware data storage arrangement 504 may be configured to support a lookup table 510 of driver command signal states (or excitation states), which may correspond to different commutation states of the stepper motor.

The selection input of the multiplexer 502 is coupled to selection logic circuitry 506 (alternatively referred to herein as select line decoding circuitry) that is configured to map or otherwise convert the commanded actuation state value provided from the duty cycle measurement logic 302 (e.g., the output of the D flip-flop circuitry 406) to a corresponding selection input for the multiplexer 502 that results in the particular set of fixed state values corresponding to the commanded actuation being provided to the driver circuitry 306 to achieve the commanded actuation of the stepper motor. In this regard, FIG. 5 includes a table 520 depicting an exemplary mapping of commanded actuation state values to selection input values (or corresponding driver command signal states) for an embodiment of the select line decoding circuitry 506. The select line decoding circuitry 506 compares the current commanded actuation state value to predetermined values (or ranges) to decode or otherwise identify the appropriate selection input state and corresponding driver command signal states for achieving the commutation state corresponding to the input duty cycle. For example, in the illustrated embodiment, in response to a commanded actuation state value between 100 and 200, the select line decoding circuitry 506 selects the set of values provided at the first input to the multiplexer 502, which results in driver command signals to turn off or disable a first switch of a first half H-bridge that is coupled between the supply voltage terminal 305 and a first motor input at a first output terminal 332, turn on or enable a second switch of the first half H-bridge that is coupled between the first output terminal 332 and a ground reference voltage node, turn on or enable a first switch of a second half H-bridge that is coupled between the supply voltage terminal 305 and a second motor input at a second output terminal 334, turn off or disable a second switch of the second half H-bridge that is coupled between the second output terminal 334 and the ground reference voltage node, turn on or enable a first switch of a third half H-bridge that is coupled between the supply voltage terminal 305 and a third motor input at a third output terminal 336, turn off or disable a second switch of the third half H-bridge that is coupled between the third output terminal 336 and the ground reference voltage node, turn off or disable a first switch of a fourth half H-bridge that is coupled between the supply voltage terminal 305 and a fourth motor input at a fourth output terminal 338, and turn on or enable a second switch of the fourth half H-bridge that is coupled between the fourth output terminal 338 and the ground reference voltage node. As illustrated, a commanded actuation state value of zero resulting from the runway prevention logic 308 in response to a static input command signal results in the driver command signals output by the multiplexer 502 grounding the output terminals 332, 334, 336, 338, thereby allowing the stepper motor to coast to a stop.

Referring to FIG. 5 with reference to FIGS. 2-5, in one or more exemplary embodiments, the actuator control module 212 may utilize the mapping between the duty cycle (or commanded actuation state value) to determine the appropriate duty cycle(s) for the input command signal provided to the input terminal 301 to achieve the rotation angle of the stepper motor 232 and thereby achieve a desired dosage of fluid delivery. For example, if the desired dosage corresponds to actuating the stepper motor 232 through two commutation states, and the sensing arrangement 216 indicates the motor 232 is in a first state (State 1), the actuator control module 212 may provide an input command signal having a duty cycle resulting in a commanded actuation state value between 300 and 400 to cause the stepper motor driver command module 500 to advance the stepper motor 232 to the next commutation state (State 2), before increasing the duty cycle to achieve a commanded actuation state value between 500 and 600 to cause the stepper motor driver command module 500 to advance the stepper motor 232 to the following commutation state (State 3), thereby actuating the stepper motor 232 through two commutation states and delivering the desired dosage. It should be appreciated that the same device package and encapsulated hardware for the electromechanical actuator driver module 300 may be employed with any number of different types of electromechanical actuators 232 and/or employed in different types or models of infusion devices 202, with the actuator control module 212 generating the input command signals provided to the actuator driver module 214, 300 according to the particular type of actuator 232 being utilized for the particular implementation.

It should be noted that FIG. 5 is a simplified representation of a driver command module for a stepper motor provided for purposes of explanation. It should be appreciated that driver command modules for other types of electromechanical actuators may be implemented in an equivalent manner to achieve the desired operation of those types of electromechanical actuators. Additionally, although FIG. 5 depicts a hardware-based implementation, alternative embodiments could utilize software to map or otherwise convert a commanded actuation state value to driver command signals, as will be appreciated in the art.

Figure 6:
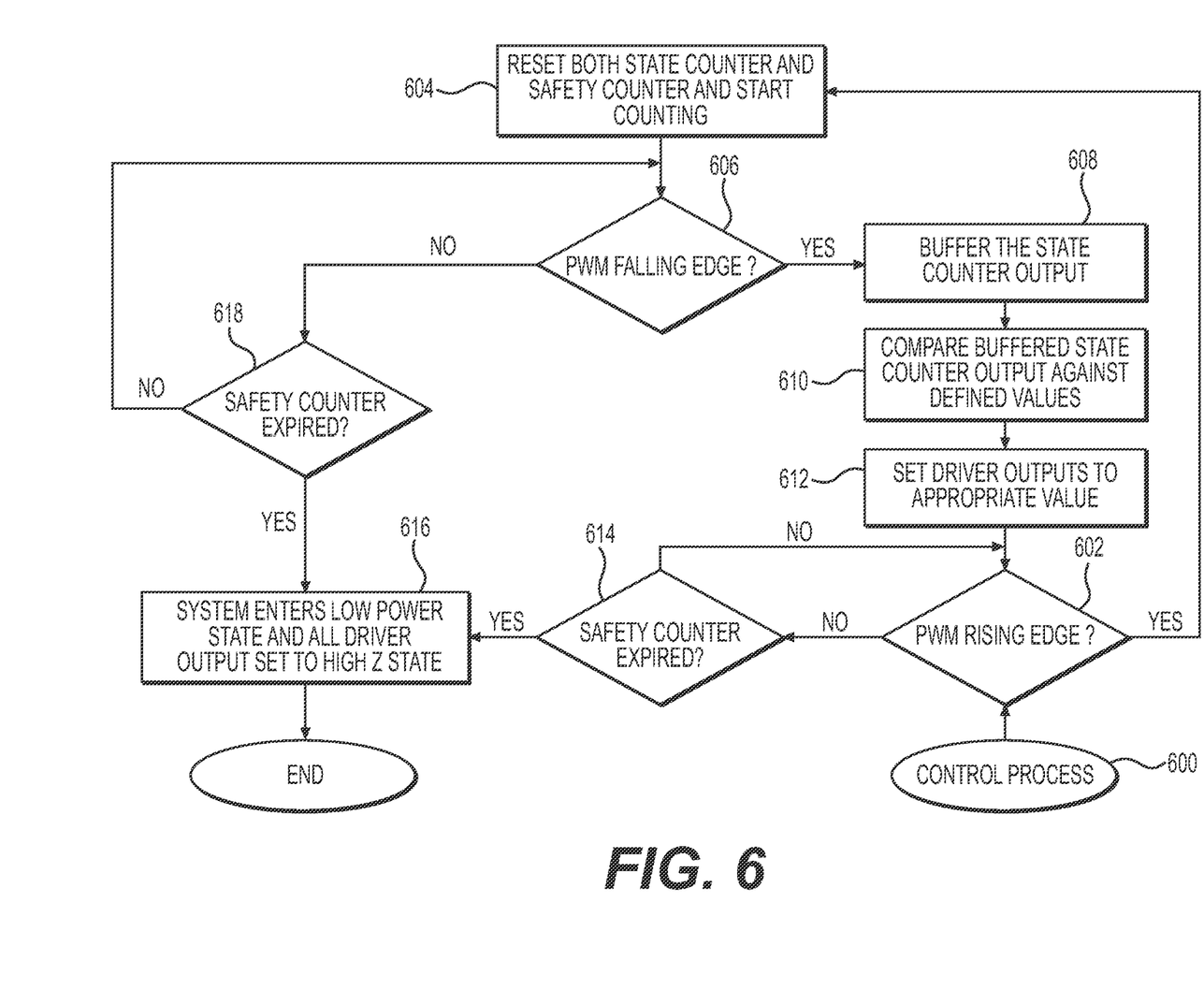
FIG. 6 is a flow diagram of an exemplary control process suitable for implementation by electromechanical actuator driver module in one or more exemplary embodiments.

FIG. 6 depicts an exemplary embodiment of a control process 600 suitable for implementation by an electromechanical actuator driver module 214, 300 to control operation of an electromechanical actuator 232. While exemplary embodiments described herein implement the control process 600 using hardware, alternative embodiments may utilize any suitable combination of electrical components, logic, firmware, and/or software executed by processing circuitry. For illustrative purposes, the following description refers to elements mentioned above in connection with FIGS. 2-5. It should be appreciated that the control process 600 may include any number of additional or alternative tasks, the tasks need not be performed in the illustrated order and/or the tasks may be performed concurrently, and/or the control process 600 may be incorporated into a more comprehensive procedure or process having additional functionality not described in detail herein. Moreover, one or more of the tasks shown and described in the context of FIG. 6 could be omitted from a practical embodiment of the control process 600 as long as the intended overall functionality remains intact.

In exemplary embodiments, the control process 600 initializes or otherwise begins in response to detecting a rising edge of an input command signal asserted or otherwise provided at an input command terminal of the electromechanical actuator driver module (task 602). In response to detecting a rising edge when the input command signal transitions to a logical high level, the control process 600 resets or otherwise initializes the state and safety counters before counting until detecting a falling edge of the input command signal (tasks 604, 606). For example, as described above in the context of FIG. 4B, the input command terminal 301 is connected to the reset inputs of the state counter 404 and the safety counter 430 to reset the values of the counters 404, 430 to zero when the signal at the input command terminal 301 transitions to a logical high voltage level.

In response to detecting a falling edge of the input command signal, the control process 600 latches or otherwise buffers the value of the state counter and then maps or otherwise converts the latched state count value to a corresponding driver output state (tasks 608, 610). For example, as described above, the input command signal from the input command terminal 301 may be inverted prior to being provided to the clock input of the D flip-flop arrangement 406 so that the D flip-flop arrangement 406 latches the value of the state counter 404 in response to a falling edge of the input command signal. The latched commanded actuation state value is then provided to the duty cycle decoding logic 304 which maps or otherwise converts the commanded actuation state value to a corresponding driver state. For example, as described above in the context of FIGS. 4-5, the driver command module 412, 414, 416, 418 for the selected type of electromechanical actuator 232 (e.g., select line decoding circuitry 506) may compare the input commanded actuation state value to predefined values or thresholds (e.g., using a lookup table 520) corresponding to different driver output states to identify the appropriate driver output state assigned to that commanded actuation state value. In this regard, in contrast to systems where the duty cycle of the command signal is correlative to or otherwise proportionally related to the amount (or percentage) of current (or power) delivered to a load during an electrical cycle, embodiments described herein map the duty cycle to a discrete commutation state (or actuation state). Thereafter, the control process 600 operates the driver circuitry of the electromechanical actuator driver module to set the voltage levels at its output terminals (which are coupled to the inputs of the electromechanical actuator) to the appropriate values for achieving the commanded actuation (task 612). For example, after mapping the commanded actuation state value to a corresponding selection input state, the select line decoding circuitry 506 operates the selection input of the multiplexer 502 to apply the driver command signals corresponding to the commanded actuation to the driver circuitry 306 to thereby set the output terminals 307 of the electromechanical actuator driver module 300 to the voltage levels for achieving the commanded actuation corresponding to the duty cycle of the input command signal.

The loop defined by tasks 602, 604, 606, 608, 610 and 612 repeats throughout operation of the electromechanical actuator 232 while the actuator control module 212 varies the duty cycle of the input command signal provided to the actuator driver module 214, 300 to achieve a desired actuation, and thereby, a desired delivery of fluid. In the absence of a rising or falling edge of the input command signal, the control process 600 monitors the value of the safety counter to detect or otherwise identify an overflow condition of the safety counter (tasks 614, 618). In response to overflow (or expiration) of the safety counter, the control process 600 disconnects the electromechanical actuator from the power supply and exits (task 616). For example, as described above, the reset input of the safety counter 430 is coupled to the input command terminal 301 and resets with the rising edge for each new cycle of the input command signal. Thus, when the input command signal is maintained at a logical high voltage or a logical low voltage, the safety counter 430 does not reset and eventually overflows. In response, the additional safety logic 432, 434 disables the oscillator circuitry 402 and sets the commanded actuation state to a zero value (e.g., by resetting the D flip-flop arrangement 406), which results in the duty cycle decoding logic 304 operating the driver circuitry 306 to disconnect the output terminals 307 from the supply voltage. In exemplary embodiments, the driver circuitry 306 is operated to provide a high impedance at the output terminals 307 and allows the electromechanical actuator 232 to coast to a stop. Thereafter, the control process 600 may be reinitiated by varying the input command signal at the input terminal (e.g., task 602), as described above.

By virtue of the subject matter described herein, various different types of electromechanical actuators may be driven using a single control signal and a common electrical hardware platform. In addition to the increased flexibility, extensibility and/or reusability of the electromechanical actuator driver module, the size of the driver module can be reduced by reducing the number of I/O interfaces required for the input commands to a single terminal. Similarly, the package size of the control module providing the input command signal can also be reduced by reducing the number of I/O interfaces required for outputting the command signal. Additionally, control signals for generating driver commands may be contained within the driver module package, leaving only a single control signal (e.g., the input command signal) exposed to environmental elements (e.g., humidity, water ingress, and/or the like) or other external factors (e.g., electromagnetic interference, electrostatic discharge, and/or the like) thereby increasing the safety. Unintentional actuation or motion of a rotor may also be inhibited by requiring a command signal at the input command terminal having a specific duty cycle (e.g., to map to a particular commanded actuation state), thereby preventing noise, transients, or other spurious signals from achieving actuation. The hardware-based implementations described herein also allows for more reliable performance that reduces software burdens and is less error prone.

For the sake of brevity, conventional techniques related to motors and related actuation systems and controls, logic circuits, electronic devices, device packaging, and other functional aspects of the subject matter may not be described in detail herein. In addition, certain terminology may also be used in the herein for the purpose of reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically. Thus, although various drawing figures may depict direct electrical connections between components, alternative embodiments may employ intervening circuit elements and/or components while functioning in a substantially similar manner.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An electromechanical actuator driver module comprising:
   a terminal to receive an input command signal;
   command logic coupled to the terminal to convert the input command signal to an actuation command; and
   decoding logic coupled to the command logic to generate a driver command for a selected type of electromechanical actuator based on the actuation command.

2. The electromechanical actuator driver module of claim 1, wherein the command logic comprises duty cycle measurement logic configured to measure a duty cycle of the input command signal to obtain the actuation command.

3. The electromechanical actuator driver module of claim 2, wherein the actuation command comprises a commanded commutation state.

4. The electromechanical actuator driver module of claim 1, wherein the decoding logic comprises:
   a plurality of driver command modules to generate a respective driver command based on the actuation command, wherein each driver command module of the plurality of driver command modules corresponds to a different one of a plurality of types of electromechanical actuators; and
   logic circuitry coupled to the plurality of driver command modules to enable a first driver command module corresponding to the selected type of actuator.

5. The electromechanical actuator driver module of claim 4, further comprising driver circuitry coupled to the decoding logic to receive the driver command output by the first driver command module.

6. The electromechanical actuator driver module of claim 5, further comprising output terminals coupled to the selected type of electromechanical actuator, wherein the driver circuitry generates output signals at the output terminals corresponding to the driver command output.

7. The electromechanical actuator driver module of claim 4, wherein the first driver command module comprises:
   a table comprising a plurality of excitation states for the selected type of actuator;
   a multiplexer coupled to the table to output a selected one of the plurality of excitation states as the driver command; and
   selection logic circuitry coupled to a selection input of the multiplexer to map the actuation command to the selected one of the plurality of excitation states.

8. The electromechanical actuator driver module of claim 1, further comprising safety logic to override the actuation command when the input command signal is constant for at least a threshold duration of time.

9. A driver module comprising:
   an input terminal to receive an input command signal having a duty cycle;
   a plurality of output terminals to be coupled to an electromechanical actuator;
   driver circuitry coupled to the plurality of output terminals;
   duty cycle measurement logic coupled to the input terminal to measure the duty cycle to obtain a commanded actuation state value; and
   duty cycle decoding logic coupled to the duty cycle measurement logic and the driver circuitry to convert the commanded actuation state value to a driver command for the electromechanical actuator and provide the driver command to the driver circuitry, wherein the driver circuitry provides output signals at the plurality of output terminals in accordance with the driver command.

10. The driver module of claim 9, wherein the electromechanical actuator comprises a selected one of a stepper motor, a brushless direct current (BLDC) motor, a brushed direct current (BDC) motor, and a shape-memory alloy actuator.

11. The driver module of claim 10, wherein the duty cycle decoding logic comprises:
   a plurality of driver command modules to generate a respective driver command based on the commanded actuation state value, wherein each driver command module of the plurality of driver command modules corresponds to a different one of a plurality of types of electromechanical actuators; and
   logic circuitry coupled to the plurality of driver command modules to enable a first driver command module corresponding to the selected one of the stepper motor, the BLDC motor, the BDC motor, and the shape-memory alloy actuator.

12. The driver module of claim 9, further comprising safety logic to set the commanded actuation state value to a default value when the input command signal is constant for at least one electrical cycle.

13. The driver module of claim 9, wherein the duty cycle decoding logic maps the commanded actuation state value to a commutation state and provides the driver command corresponding to the commutation state to the driver circuitry.

14. The driver module of claim 9, wherein the driver circuitry, the duty cycle measurement logic, and the duty cycle decoding logic are encapsulated in a common device package including the input terminal and the plurality of output terminals.

15. A method of controlling an electromechanical actuator in response to an input command signal at an input terminal, the method comprising:
   determining a commanded actuation state value based on a characteristic of the input command signal;
   generating driver command signals based on the commanded actuation state value and an actuator type associated with the electromechanical actuator; and
   operating driver circuitry in accordance with the driver command signals to provide output signals at output terminals coupled to the electromechanical actuator.

16. The method of claim 15, wherein determining the commanded actuation state value comprises measuring a duty cycle of the input command signal.

17. The method of claim 16, further comprising disabling actuation of the electromechanical actuator when the input command signal is constant.

18. The method of claim 17, wherein disabling actuation comprises setting the commanded actuation state value to a default value that results in the driver command signals providing an impedance at the output terminals.

19. The method of claim 15, further comprising:
   identifying the actuator type as being selected from among a plurality of actuator types associated with a driver module comprising the input terminal and the output terminals; and
   enabling a driver command module associated with the actuator type to generate the driver command signals based on the commanded actuation state value.

20. The method of claim 19, wherein the plurality of actuator types comprises one or more of a stepper motor, a brushless direct current (BLDC) motor, a brushed direct current (BDC) motor, and a shape-memory alloy actuator.

* * * * *